(12) United States Patent
Demarest et al.

(10) Patent No.: US 7,038,779 B2
(45) Date of Patent: May 2, 2006

(54) SYSTEM AND METHOD FOR SENSING VARIATIONS IN A STRAND

(75) Inventors: David D. Demarest, Parsippany, NJ (US); Michael D. Prikril, Cliffwood Beach, NJ (US); William F. Smith, Ringoes, NJ (US)

(73) Assignee: Ethicon Inc., Somerville, NJ (US)

( * ) Notice: Subject to any disclaimer, the term of this patent is extended or adjusted under 35 U.S.C. 154(b) by 360 days.

(21) Appl. No.: 10/683,497

(22) Filed: Oct. 10, 2003

(65) Prior Publication Data

US 2005/0078313 A1  Apr. 14, 2005

(51) Int. Cl.
*G01N 21/84* (2006.01)

(52) U.S. Cl. .................... 356/430; 356/238.2
(58) Field of Classification Search ............... 356/430; 250/559.01
See application file for complete search history.

(56) References Cited

U.S. PATENT DOCUMENTS

| | | | |
|---|---|---|---|
| 3,922,093 A * | 11/1975 | Dandliker et al. ......... 356/600 |
| 3,983,388 A | 9/1976 | Gugliotta | |
| 4,109,594 A | 8/1978 | Spanel et al. | |
| 4,538,536 A | 9/1985 | Sick | |
| 4,625,666 A | 12/1986 | Sick | |
| 4,691,647 A | 9/1987 | von Stein | |
| 4,802,762 A | 2/1989 | Hill, Jr. | |
| 5,109,236 A * | 4/1992 | Watanabe et al. ........... 347/193 |
| 5,521,707 A | 5/1996 | Castore et al. | |
| 5,588,428 A | 12/1996 | Smith et al. | |
| 5,712,706 A | 1/1998 | Castore et al. | |
| 5,778,724 A * | 7/1998 | Clapp et al. ................. 73/159 |
| 6,041,020 A | 3/2000 | Caron et al. | |

OTHER PUBLICATIONS

Engineering Takikawa Precision Non-Contact Measurement Products, TM-503W Operation/Maintenance Manual.
Research Disclosure Journal, ISSN 0374-4353, Mar. 2000, Research Disclosure Database No. 431047, Kenneth Mason Publications, Ltd. Westbourne, Hants., UK, Anonymous, "Continuous laser inspection of monofilament surgical sutures."

* cited by examiner

*Primary Examiner*—Gregory J. Toatley, Jr.
*Assistant Examiner*—Roy M. Punnoose
(74) *Attorney, Agent, or Firm*—Emil Richard Skuls

(57) ABSTRACT

A system for monitoring production of uniform strands, such as medical sutures, utilizes a measurement head through which the strand passes. The measurement head includes a plurality of light beams illuminating a corresponding number of sensors. The light beams all illuminate the same section of the strand as it travels through the measurement head. Passage of a fault through the light beams produces a fault signal, which is used by the production system to excise and discard the strand section including the fault. Synchronization and summing of the plurality of fault signals increases the sensitivity and accuracy of the system.

18 Claims, 5 Drawing Sheets

SYSTEM AND METHOD FOR SENSING VARIATIONS IN A STRAND

FIELD OF THE INVENTION

The invention is an inspection method and system for detecting flaws in a cylindrical strand.

BACKGROUND OF THE INVENTION

Systems for optical inspection of strands, such as thread, optical fiber and polymer filaments are known. One such sensing head utilizing three noncolinear light beams is marketed by Takikawa Engineering of Tokyo, Japan. In this system the three light beams are detected after being incident on the strand being monitored and each signal is monitored to produce an alarm signal if the monitored signal exceeds a threshold indicating the presence of an unacceptably large fault. For demanding, high tolerance applications, such as sutures to be used in heart operations, systems of greater sensitivity are desired.

SUMMARY OF THE INVENTION

The disclosed invention is an optical inspection system for effectively detecting defects in cylindrical strands, such as monofilament surgical suture materials. The system described is capable of detecting defects such as: nicks, bumps, scrapes, abrupt neck-downs, splits, frays, contamination (dust), as well as internal voids and color variation.

One objective of this system is to provide a highly reliable method of high-speed continuous detection of micron-sized defects in monofilament surgical suture material. Resulting benefits associated with this system include improved product consistency and quality, reduced product costs, and facilitating integration with collateral automation processes, such as in-line suture annealing and automated cutting. The exemplary optical inspection system discussed here utilizes a three-beam LED scanning head and digital signal processing systems.

The first subsystem is a three-beam infrared light emitting diode scanning head. For this exemplary application, this subsystem was set up to detect surface anomalies in the range of from about 10 uM (0.0004") to about 25 uM (0.001"). The unit was mounted with the (3) optical beams normal to the thread path, approximately equally spaced circumferentially about the strand's axis.

The Digital Signal Processing (DSP) subsystem unit comprises application specific software and data collection hardware. The software functions as an operator interface, controls the application, collects and interprets data, digitally processes analog sensor signals through application of mathematical algorithms, and displays information. Data collection is accomplished through computer-mounted, commercially available data collection cards, such as Item #NI DAQ, available from Labcon, Corp. of San Diego, Calif. An operational overview of the DSP is as follows:

Data from each axis of the three-beam infrared light emitting diode scanning head is consolidated into a single composite signal, reducing signal noise. This results in tighter detection thresholds.

Signal symmetry is adjusted about the zero axis by mathematically removing all DC components from the signal. This centers the signal around the zero axis and allows symmetrical positioning of positive and negative thresholds.

Software selectable detection thresholds are established above the signal noise base. Signal peaks above these thresholds trigger defect outputs.

A sensor failure detection function is incorporated to trigger shut down and alarm if sensor input is lost.

Optional surface roughness tracking, as well as Statistical Process Control (SPC) charts can be incorporated.

The system can be configured network-ready for remote data collection.

Outputs are configured for Programmable Logic Controllers (PLC) and Robot control with a 24VDC logic interface.

The increased sensitivity and reproducibility is achieved, primarily, through synchronizing the outputs of the three axes and summing them to produce a single monitoring output. Synchronization is done mechanically, electronically, or by a combination of the techniques. The mechanical synchronization is accomplished through placement of one or more shims in the mounts of either the light emitting diodes or the sensors detecting the optical signals such that the three beams are illuminating the same section of the strand. In an exemplary system this adjustment produced beam coincidence to within approximately 0.002 inches.

Synchronization can be done electronically by placing an electronic time delay device in each signal leg to adjust the signal paths to within approximately 30 microseconds. A combination of these two techniques can be applied, for example, by utilizing the mechanical technique during initial system set up and the electronic technique to correct system drift detected during periodic alignment checks.

The system prototype was tested on a servo driven test strand, which re-circulates a continuous loop of suture material with known defects, through all sensor units. The purpose of the test strand set up was to validate repeatability of all system components.

By combining a system of sensors with sophisticated data collection and signal processing software, a broadened spectrum of potential suture defects are detectable, both in defect type and size. The system is capable of detecting external defects, typically, but not limited to: nicks, bumps, scrapes, abrupt neck-downs, splits, frays, contamination (dust), as well as internal defects, typically voids and color variation. The system has shown to meet or exceed sensitivity equivalence with human tactile and visual capabilities for critical suture inspections, while additionally providing statistical process control and repeatability. Variations of the system are applicable to the wire, textile and fiber optic industries.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE INVENTION

Figure 1A:
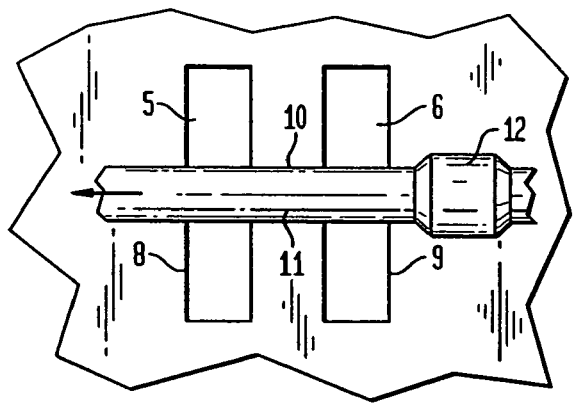
FIGS. 1a and 1b are elevational views which schematically illustrate the passage of a fault in front of the two slits in the mask covering a sensor.

FIGS. 1a, 1b, 2a and 2b illustrate how defects can be detected in a continuous strand (10) by interposing the strand (10) between a light source, such as an LED and a pair of sensing elements (5, 6) shielded by mask (7). The mask (7) has a pair of parallel slits (8, 9), e.g., about 100 micrometers wide, delimiting the light (13) projected therethrough.

Figure 1B:
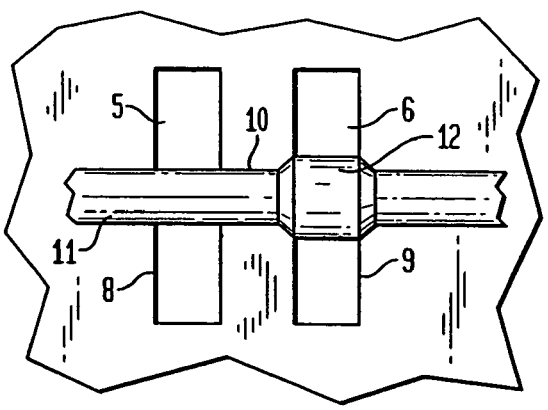

When a uniform portion (11) of the strand (10) is passed in front of the parallel slits (8, 9) covering light sensing elements (5, 6), as illustrated in FIGS. 1a, 1b, the difference in the amount of light received by sensing elements (5, 6) is null. When a lump or bump (12), i.e., a flaw, is passed across the slits (8, 9), the amount of light received by sensing elements (5, 6) becomes unbalanced. The difference is in proportion to the size of the flaw 12, i.e, lump/bump, in the strand (10). When this difference exceeds a preset value, an alarm signal is output.

If this type of detection apparatus is used for primary or secondary glass fiber or other translucent or transparent materials, the system can also detect small internal inclusions, bubbles and cracks. Light (13) penetrates through the material, but internal defects interrupt the light pattern due to refractions in the glass. This change causes a difference in the amount of light received by the sensing elements (5, 6) which causes an alarm output.

Figure 2A:
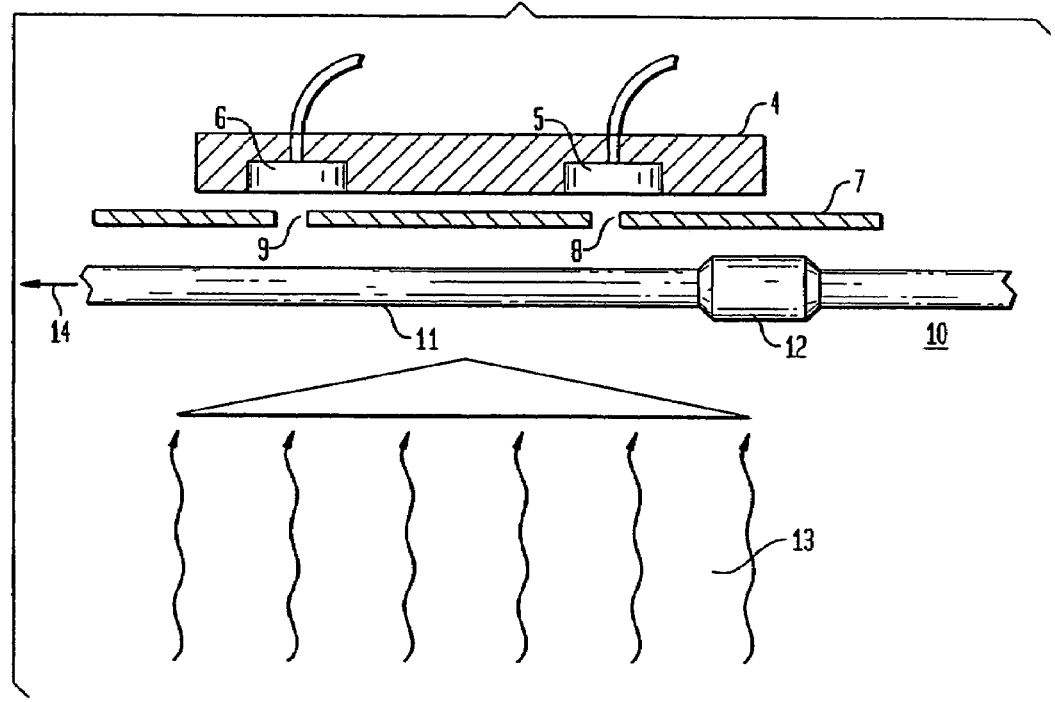
FIGS. 2a and 2b are top views, in section, showing the two sensing elements in a sensor and how the illumination of each of element changes as a fault passes in front of the two slits.
Figure 2B:
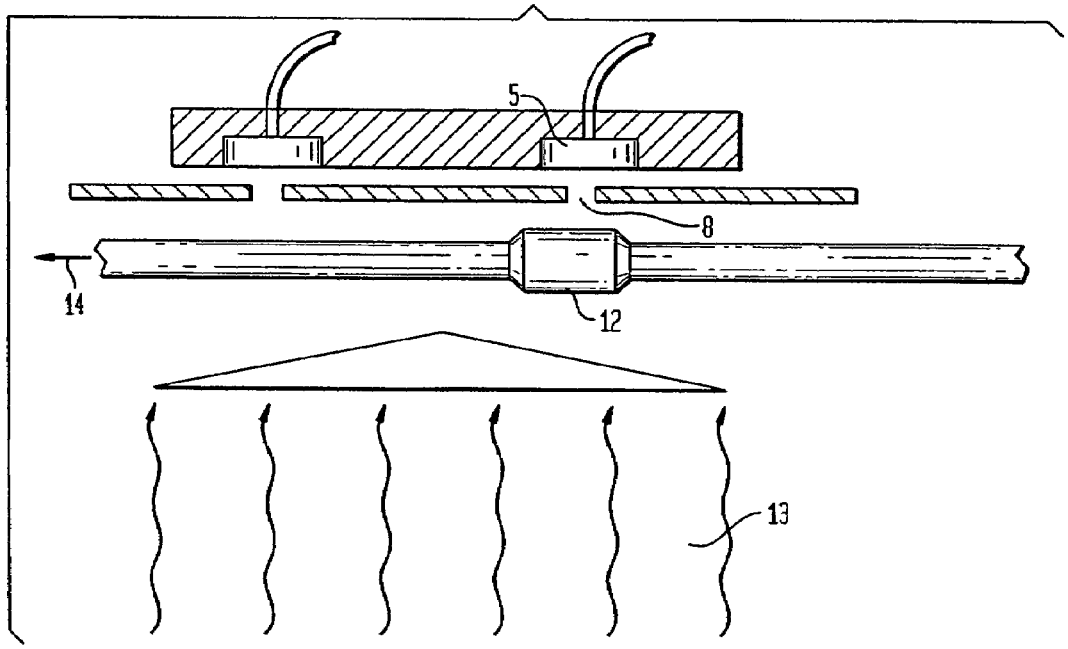

FIG. 2a shows a sensor (4) with two sensing elements (5, 6) behind a mask (7) defining two slits (8, 9). The strand being inspected (10) has a uniform section (11) and a bump fault (12). A light beam (13) illuminates the strand (10) and the slits (8, 9) distal of the strand (10). In the figure, the uniform section (11) of the strand is in front of both slits (8, 9) intercepting equal amounts of light from the light beam (13), producing equal signals in the sensing elements (5, 6) and a null in the external circuitry. In FIG. 2b, the fault (12) has progressed in the direction of the arrow (14) and changes the amount of light falling on sensing element (5) through slit (8), producing an unbalance signal in the external circuitry and a fault signal.

Figure 3:
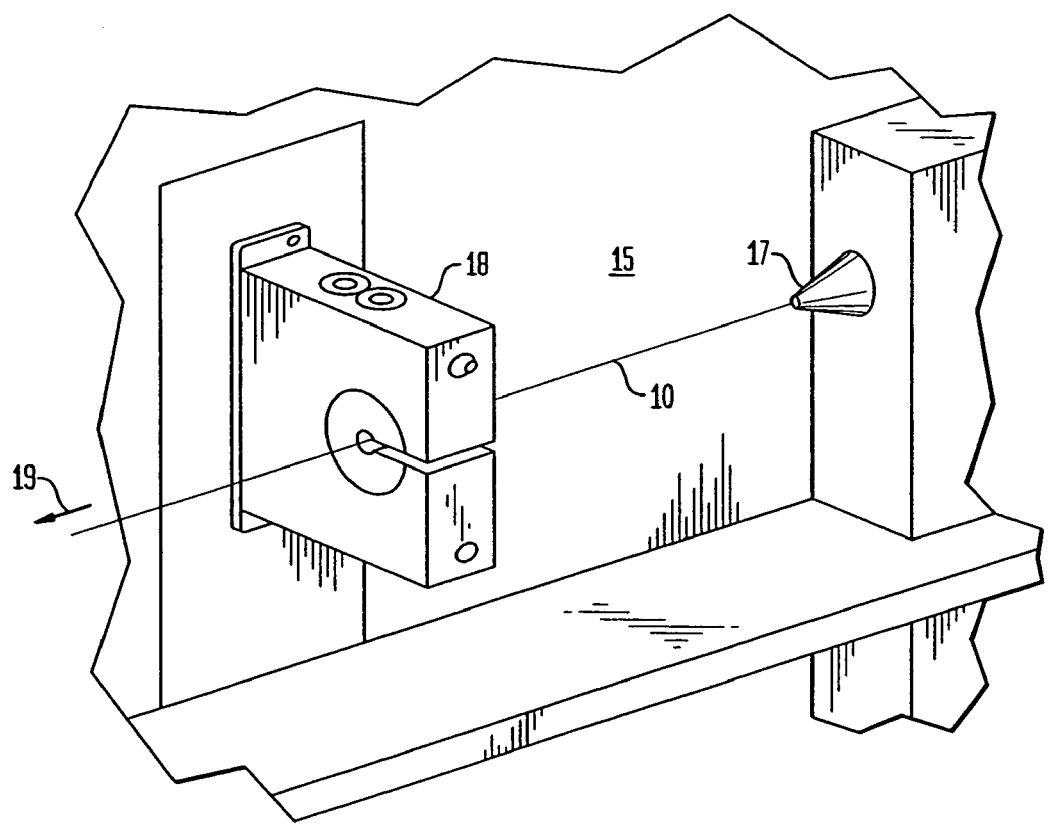
FIG. 3 is a perspective view of a portion of a production system, showing a strand passing through a sensing head.

FIG. 3 shows a portion (15) of a production system in which a strand (10) being produced and monitored is fed from a feed head (17) and passed through a sensing head (18) as it proceeds in the direction indicated by the arrow (19) through the remainder of the production system. An automated production system might include a counting wheel to correlate a fault signal with a position on the strand so that the fault could be excised by automated cutting equipment. If the cutting equipment is set to cut the strand to preset lengths, data from the counting wheel would identify the particular length possessing the fault, which could be automatically rejected. The production system could also store the location of the fault in a memory for later use in excising the fault.

Figure 4:
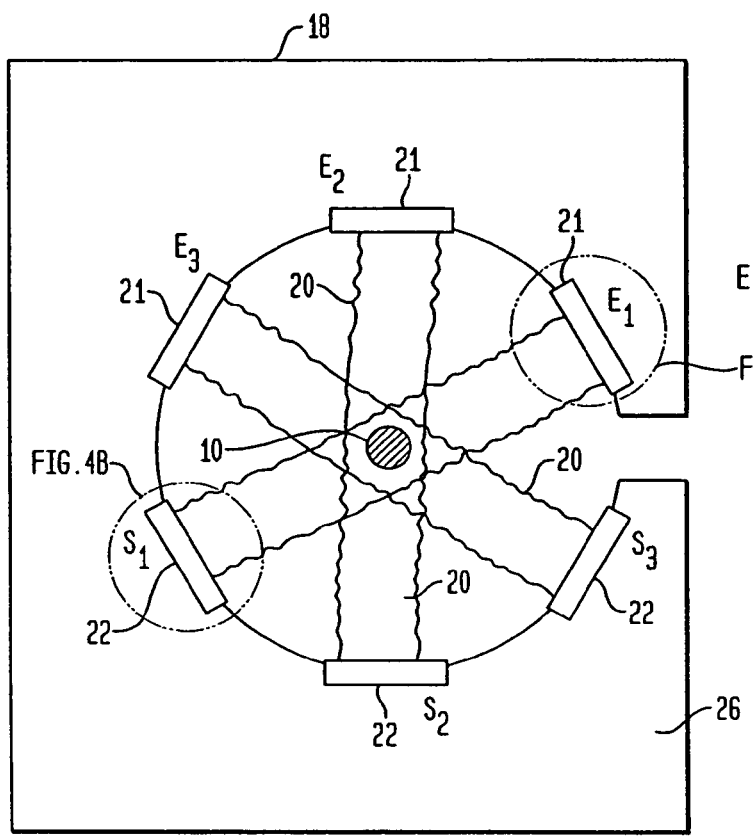
FIG. 4 is an elevational view of a sensing head showing three non-colinear light beams and details of an exemplary sensor and an exemplary emitter.
Figure 4A:
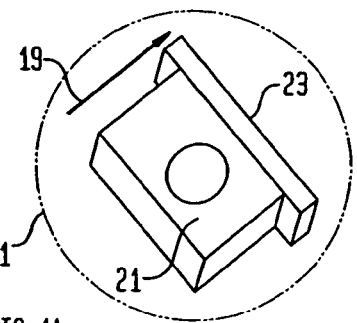
Figure 4B:
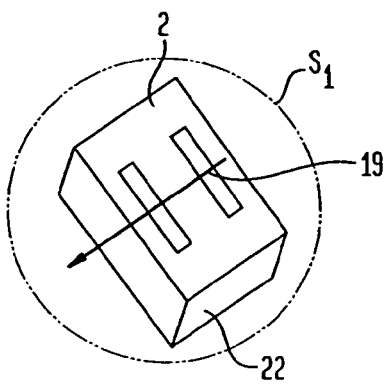

The exemplary sensing head (18) illustrated in more detail in FIG. 4 incorporates three non-colinear light beams generated by three emitters (21) and detected by three sensors (22). The light beams are disposed with approximately equal angular separation. In an exemplary device, near infrared LEDs operating at a wave length of approximately 720 nm were used. In order to accomplish mechanical synchronization, a spacer or "shim" (23) is used to shift the sensor (21) in the axial direction. In this exemplary system, it was determined that a shift of 0.001 inches (one mil) produced approximately a twenty microsecond synchronization shift during the calibration procedure. The arrows (19) indicate the direction of motion of the strand (16), as illustrated in FIG. 3.

The sensor (22) is covered by a mask (24) defining two slits (25). As illustrated, the slits (25) are perpendicular to the direction of motion (19) of the strand, perpendicular to the corresponding light beam (20) and parallel to the measurement plane, defined by the broad surface (26) of the sensing head (18). An exemplary system employed 100 micrometer wide slits separated by approximately three millimeters.

Figure 5A:
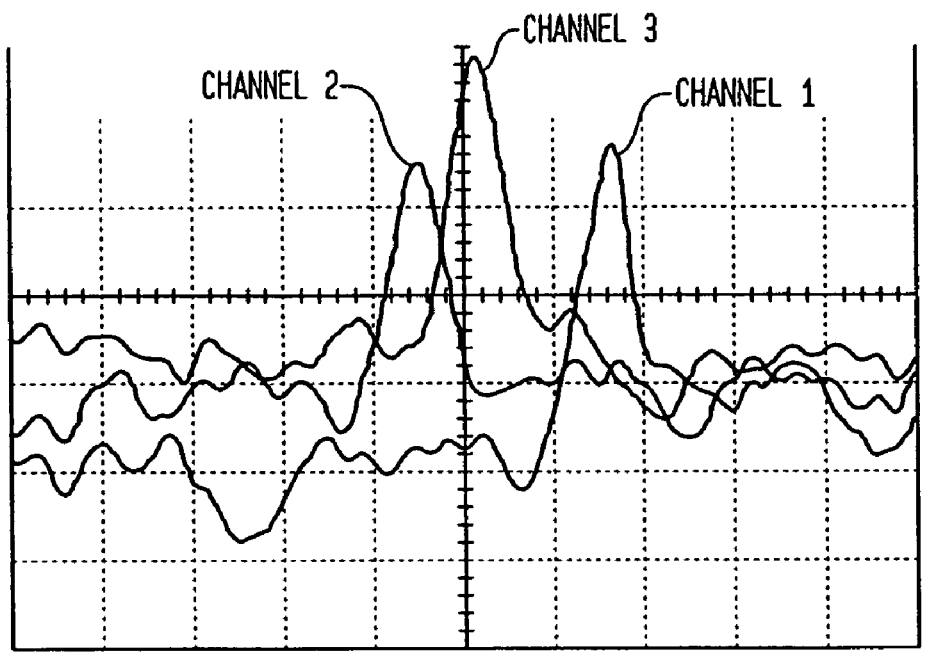
FIGS. 5a and 5b are sets of curves showing the inspection signals from the three sensors before (5a) and after (5b) synchronization.
Figure 5B:
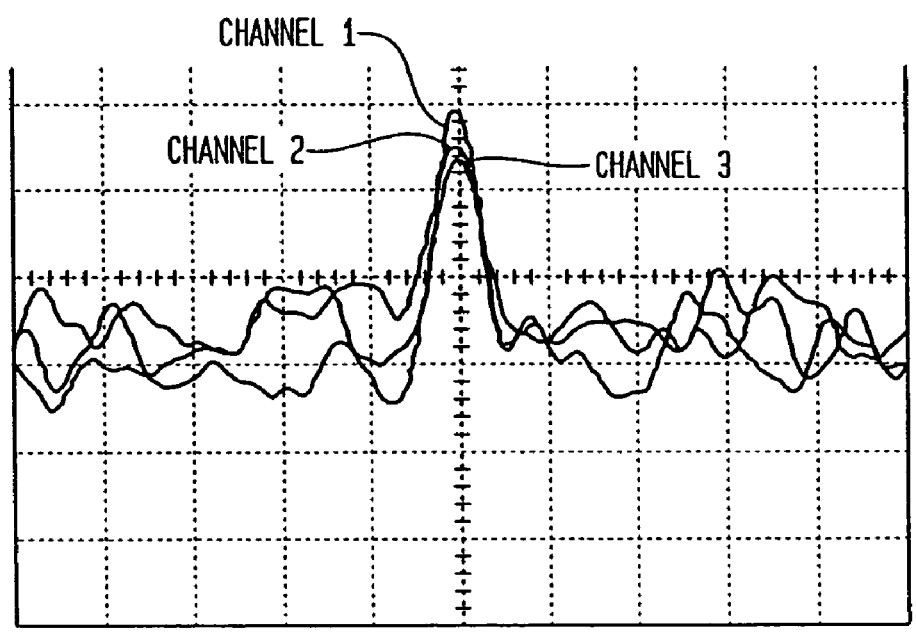

FIG. 5 shows oscilloscope traces of inspection signals produced by the three sensors (22), labeled channels 1, 2, and 3 observing a sixteen micrometer deep groove in a test pin. FIG. 5a, taken before mechanical synchronization, shows a maximum offset of approximately 200 microseconds in the three fault signals. After placement of appropriate shims, FIG. 5b shows the channels synchronized to within 30 microseconds. With this degree of synchronization, addition of the three inspection signals produces reinforcement of the fault signals and averaging of the surrounding noise signals.

Figure 6:
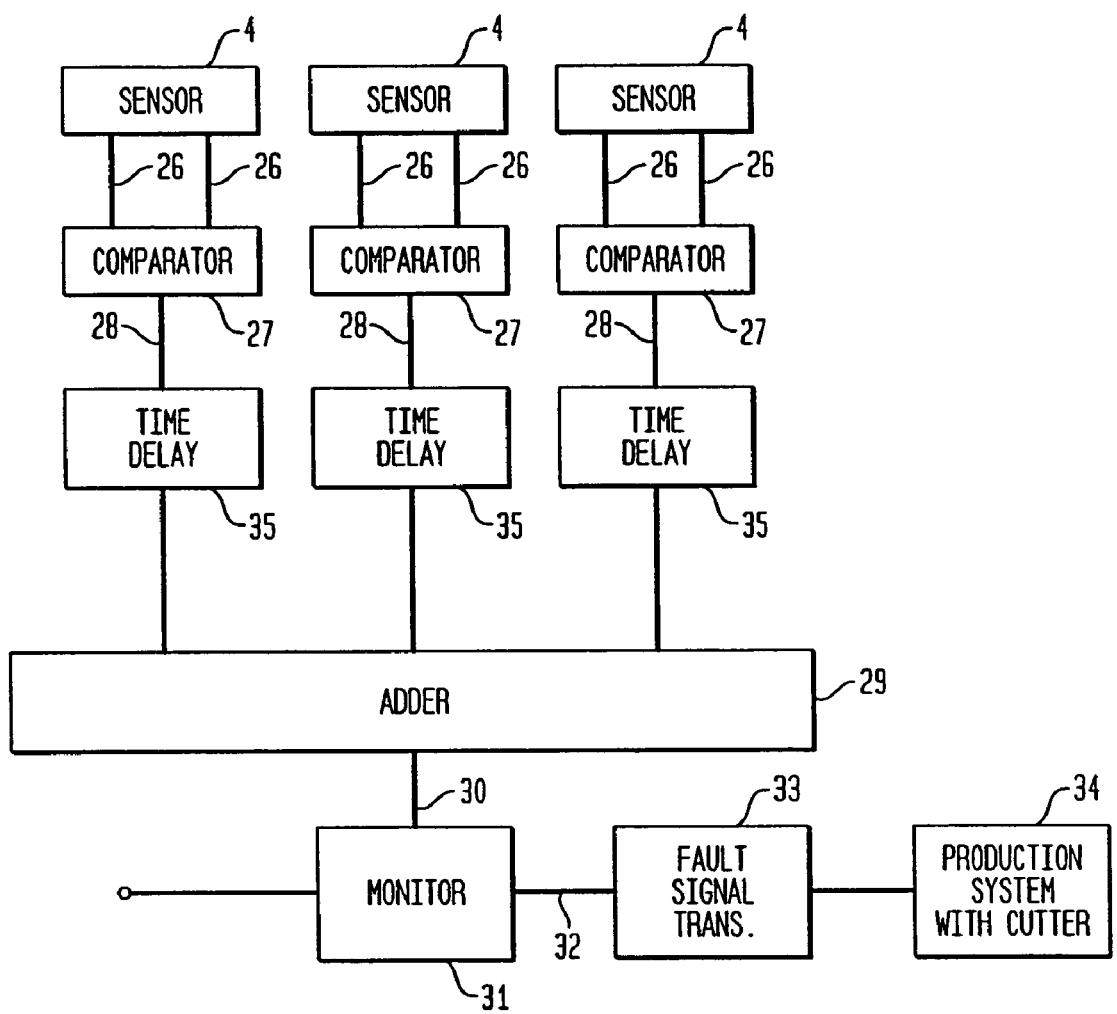
FIG. 6 is a schematic representation of the signal processing portion of an exemplary system of the invention.

FIG. 6 is a block diagram schematically representing the signal processing elements of an exemplary system of the invention. Each sensor (e.g., 4 of FIG. 2) produces two sensing signals (26) that are passed into a comparator (27). Each comparator (27) is balanced to a null at the noise level when a uniform section of the strand passes across the two slits of the sensor. Each sensing signal is produced by one of the sensing elements (5, 6) behind one of the slits (8, 9). When a fault (12) in the strand passes in front of one of the slits (8) the fault intercepts a different amount of light than the uniform part of the strand and an unbalance is produced in the comparator (27), resulting in a fault condition in the inspection signal at the output (28) of each comparator (27).

If the fault is asymmetric, such as a lump or nick on one side of the strand, the inspection signals may not be equal. However, synchronization of the inspection signals assures that when combined in the adder (29), the resulting monitoring signal (30) accurately reflects the magnitude of the fault. It should be appreciated that many flaws will cause a signal variation in at least two of the sensing elements (5, 6). For example, a necked-down portion of the strand (16) that is directly sensed (in profile) by a first sensing element, e.g., (5), may be indirectly sensed by a second sensing element, e.g., (6), due to a greater eight transmissivity of the necked-down portion. This cumulative effect enhances the sensitivity of the present invention due to the aforesaid sensing upon a uniform section (11) of the strand (10) and adding the individual signals. The monitor (31) then compares the monitoring signal (30) to a preselected fault threshold, which produces a fault signal (32). The fault signal (32) is carried by a fault signal transmitter (33) to the strand production system (34).

The production system (34) either includes an automated cutter adapted to excise and discard the section of strand that includes the fault or a counting wheel (or other mechanical locater device) with an electronic output that feeds memory that records the location of the fault for later processing to excise the fault.

As an alternative, or in addition to, mechanical synchronization, the inspection signals can be synchronized by insertion of a time delay device (35) in each channel to synchronize the signals passing into the adder (29). It may be efficient, for example, to mechanically synchronize the sensor head (18) during initial system set up or periodic major overhaul and trim the synchronization electronically during daily or weekly recalibration.

It must be realized that objectives of this invention can be accomplished in many ways employing the fundamental synchronization and addition teaching disclosed herein. Further, that as used herein, the term "cylindrical" is used in the broadest sense and includes the linear translation of any regular closed geometric figure, such as a circle, square or hexagon. The individual functional elements are all well known in the art. The signal processing and logic can be accomplished through analog or digital methods, as desired by the system developer.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

We claim:

1. A method for detection of a fault in an otherwise uniform cylindrical strand traveling in an axial direction parallel to the strand's axis and perpendicular to a measurement plane, comprising:
    a) illuminating the strand with at least a first and a second non-colinear light beam projected in a measurement plane perpendicular to the axial direction from at least a first and a second emitter, the light beams being incident, respectively, on a first and a second sensor distal of the strand, producing at least a first and a second inspection signal in a first and a second signal path;
    b) synchronizing the inspection signals;
    c) summing the inspection signals; and
    d) sensing a fault condition and producing a fault signal.

2. The method of claim 1, further comprising synchronizing the inspection signals by positioning at least one of the first and second emitter, such that the light beams illuminate the same position on the strand, within an axial distance tolerance.

3. The method of claim 2, wherein said step of positioning includes inserting a spacer next to at least one of the first and second emitter and the first and second sensor.

4. The method of claim 1, further comprising synchronizing the inspection signals by inserting a time delay in at least one of the first and the second signal paths.

5. The method of claim 1, in which there are three non-colinear light beams in the measurement plane.

6. The method of claim 5, in which the angular separations between the three light beams are approximately equal.

7. The method of claim 1, further comprising positioning within each sensor a first and a second sensing element placed, respectively, behind a first and a second narrow slit, said slits extending perpendicular to the axis of the strand and lying in the measurement plane, whereby a fault passing in front of the first slit and then in front of the second slit produces a difference between the first and second sensing element outputs; comparing the outputs to produce the inspection signal in each sensor; summing the inspection signals from the at least first and second sensors to produce a monitoring signal; and comparing the monitoring signal to a preselected fault threshold, whereby the fault signal is produced when the monitoring signal exceeds the fault threshold when a fault passes through the light beams.

8. The method of claim 1, further comprising correlating the fault signal with the fault's location on the strand and recording the fault's location in a memory.

9. The method of claim 1, wherein said fault detection method is exercised in a production system and further including the step of transmitting the fault's location to the production system.

10. The method of claim 1, further comprising the step of excising the fault from the strand.

11. A system for detection of a fault in an otherwise uniform cylindrical strand traveling in an axial direction parallel to the strand's axis and perpendicular to a measurement plane, in a production system, comprising:
    a) a sensing head with a plurality of non-colinear light beam emitters and a light beam sensors, each light beam emitter positioned to illuminate the strand and its corresponding sensor distal of the strand, and each sensor producing an inspection signal;
    b) an adder for summing synchronized inspection signals and producing a monitoring signal corresponding to the strand's uniformity; and
    c) a monitor incorporating a preselected fault threshold and adapted to produce a fault signal when the monitoring signal exceeds the fault threshold.

12. The system of claim 11, further comprising a transmitter for transmitting the fault signal to the production system.

13. The system of claim 11, further comprising a memory for recording the fault's position on the strand.

14. The system of claim 11, further comprising a cutter for excising the fault.

15. The system of claim 11, in which the sensing head comprises at least one spacer, in contact with at least one emitter or sensor, adapted for synchronizing the inspection signals by assuring that the light beams converge to illuminate a single section of the strand, within a preselected tolerance.

16. The system of a claim 11, further comprising at least one time delay device, in at least one inspection signal path, adapted for synchronizing the inspection signals.

17. The system of claim 16, further comprising a time delay device, in each inspection signal path, adapted for synchronizing the inspection signals.

18. The system of claim 11, in which each sensor comprises two sensing elements arrayed along the strand's axis and behind a mask defining a first and a second slit and producing two sensing signals, such that when a fault passes in front of the first slit and then in front of the second slit, a difference in the sensing signals is produced, the system further comprising a comparator for comparing the two sensing signals and producing the inspection signal.

* * * * *